United States Patent
Blankenship et al.

(10) Patent No.: US 6,936,568 B2
(45) Date of Patent: Aug. 30, 2005

(54) SELECTIVE HYDROGENATION CATALYST

(75) Inventors: Steven A. Blankenship, Radcliff, KY (US); Andrzej Rokicki, Prospect, KY (US); Jennifer A. Perkins, Crestwood, KY (US)

(73) Assignee: Sud-Chemie Inc., Louisville, KY (US)

( * ) Notice: Subject to any disclaimer, the term of this patent is extended or adjusted under 35 U.S.C. 154(b) by 408 days.

(21) Appl. No.: 10/170,710

(22) Filed: Jun. 12, 2002

(65) Prior Publication Data

US 2003/0232719 A1 Dec. 18, 2003

(51) Int. Cl.$^7$ .......................... B01J 23/58; B01J 21/00; B01J 23/40; B01J 23/42; B01J 23/44
(52) U.S. Cl. ................ 502/330; 502/243; 502/327; 502/332; 502/333; 502/334; 502/339; 502/344
(58) Field of Search .............................. 502/243, 261, 502/262, 263, 320, 327, 329, 330, 332–335, 339, 344, 349–351, 355, 415, 439, 524

(56) References Cited

U.S. PATENT DOCUMENTS

| | | | |
|---|---|---|---|
| 4,087,622 A | | 5/1978 | Nakamura |
| 4,477,590 A | * | 10/1984 | Kresge et al. ............... 502/334 |
| 4,480,050 A | * | 10/1984 | Brennan ...................... 502/330 |
| 4,522,792 A | * | 6/1985 | Brennan ................... 423/213.5 |
| 4,650,782 A | * | 3/1987 | Onal ........................... 502/339 |
| 5,693,586 A | * | 12/1997 | Nicolau et al. .............. 502/330 |
| 5,700,753 A | * | 12/1997 | Wang et al. ................. 502/330 |
| 5,877,350 A | * | 3/1999 | Langer et al. ............... 564/423 |
| 6,013,834 A | * | 1/2000 | Colling ....................... 560/245 |
| 6,022,823 A | | 2/2000 | Augustine et al. |
| 6,114,573 A | | 9/2000 | Herzog |
| 6,204,218 B1 | | 3/2001 | Flick et al. |
| 6,303,537 B1 | | 10/2001 | Wang et al. |
| 6,350,717 B1 | * | 2/2002 | Frenzel et al. ............... 502/330 |
| 6,420,308 B1 | * | 7/2002 | Khanmamedova .......... 502/344 |
| 6,603,038 B1 | * | 8/2003 | Hagemeyer et al. ..... 560/241.1 |
| 2003/0023121 A1 | | 1/2003 | Frenzel et al. |

FOREIGN PATENT DOCUMENTS

| | | |
|---|---|---|
| WO | WO 01/41922 | 6/2001 |
| WO | WO 02/078839 A1 | 3/2002 |
| WO | WO 02/081416 A2 | 3/2002 |

* cited by examiner

*Primary Examiner*—Cam N. Nguyen
(74) *Attorney, Agent, or Firm*—Scott R. Cox; Joan L. Simunic

(57) ABSTRACT

A catalyst for selective hydrogenation of acetylene including a high surface area support material with a surface area at least about 150 m$^2$/g and gold wherein the gold comprises from about 0.05 to about 5.0 weight percent of the catalyst and wherein the depth of penetration of the gold into the support material is such that at least about 90 percent of the gold is located within about 250 microns of the surface of the catalyst. A noble metal additive may also be included in the gold catalyst.

20 Claims, No Drawings

SELECTIVE HYDROGENATION CATALYST

CROSS REFERENCE TO RELATED APPLICATIONS

NONE

BACKGROUND OF INVENTION

1. Field of Invention

This invention relates to selective hydrogenation catalysts, more particularly to a gold impregnated catalyst with a high surface area carrier, the catalyst being useful for the selective hydrogenation of acetylene in an olefinic feed stream, particularly for ethylene purification. This invention also relates to processes of preparation and use of these catalysts.

2. Prior Art

The manufacture of unsaturated hydrocarbons usually involves cracking various types of hydrocarbons. This often produces a crude product containing hydrocarbon impurities that are more unsaturated than the desired product. An example of this problem occurs with ethylene purification processes, in which acetylene is a common impurity. An example of the process of ethylene purification is described in UK Patent No. 802,100. These unsaturated hydrocarbon impurities are often very difficult to completely remove by fractionation from the desired product. Further, it is often difficult, industrially, to hydrogenate the highly unsaturated hydrocarbon impurities without significant hydrogenation of the desired unsaturated hydrocarbons also occurring.

Two general types of gas phase selective hydrogenation processes for removing undesired, unsaturated hydrocarbons are commonly used: "front-end" hydrogenation and "tail-end" hydrogenation. "Front-end" hydrogenation involves passing the crude gas from the initial cracking step, after removal of steam and condensible organic material, over a hydrogenation catalyst. The crude gas generally includes a relatively large volume of hydrogen and a mixture of unsaturated hydrocarbons. Typically, the hydrogen gas concentration is greater than the stoichiometric amount needed for complete hydrogenation of the acetylenes present in the crude gas. To minimize the risk of the excess hydrogen gas hydrogenating ethylene in the feed stream, the hydrogenation catalyst must be very selective. Further, the catalyst risks being damaged in the front-end reactions because hydrogenation of ethylene can lead to thermal excursion, known as "run-away" whereby high temperatures are experienced. Run-away can also result in severe loss of ethylene.

In "tail-end" hydrogenation, the crude gas is fractionated prior to hydrogenation resulting in concentrated product streams. Hydrogen is then added to these product streams, if necessary, such that a slight excess of hydrogen is present over the quantity required for complete hydrogenation of the acetylenes. Tail-end reactor systems generally operate at lower GHSV of 2500–5000 per bed. In tail-end systems there is a greater tendency for deactivation of the catalyst, and consequently, periodic regeneration of the catalyst is necessary. While the quantity of hydrogen added can be adjusted to maintain selectivity, formation of polymers is a major problem in these systems.

One type of catalyst that is preferred for these selective hydrogenation reactions is comprised of palladium supported on a low surface area substrate, such as a low surface area alumina. However, one of the problems with supported palladium catalysts is that under normal operating conditions not only is the acetylene hydrogenated, but a substantial portion of the ethylene is also converted to ethane. In addition, these palladium on alumina catalysts often have relatively low stability over extended periods of time due to the formation of large quantities of oligomers on the catalyst surface.

Enhancers are often added to the palladium to improve the catalyst's properties. Copper, silver, gold, germanium, tin, lead, rhenium, gallium, indium, and thallium have been proposed as enhancers or modifiers for palladium hydrogenation catalysts. For example, acetylene hydrogenation catalysts for ethylene purification comprising palladium with a silver additive on a low surface area support material are disclosed in U.S. Pat. Nos. 4,404,124, 4,484,015, 5,488,024, 5,489,565 and 5,648,576. Specifically, U.S. Pat. No. 5,648,576 discloses a selective hydrogenation catalyst for acetylene compounds comprising from about 0.01 to 0.5 weight percent of palladium and, preferably, from about 0.001 to 0.02 percent by weight of silver. Eighty percent (80%) or more of the silver is placed within a thin layer near the surface of the carrier body. Catalysts containing palladium and Group IB metals (Cu, Ag, Au) on alumina used for the hydrogenation of acetylenes and diolefins have been suggested by G.B. 802,100 and U.S. Pat. No. 5,648,576. However, the emphasis of these patents is on silver promotion of palladium and the inclusion of copper and gold in the patents is, by and large, coincidental. U.S. Pat. Nos. 4,490,481 and 4,533,779 disclose palladium catalysts promoted with gold for the hydrogenation of acetylenes and dienes. In the '481 and '779 catalysts, the palladium is present at a significantly higher concentration than the gold. (See also U.S. Pat. Nos. 4,571,442, 4,587,369 and 5,059,732). The catalyst supports for these catalysts have a surface area less than 150 $m^2/g$ and generally less than 100 $m^2/g$.

Gold has been recognized as an active catalyst component only fairly recently. Due to its weak chemisorbtion properties, gold has been long believed to be catalytically inactive and consequently its use has remained largely unexplored (G. C. Bonn, "Gold: A relatively New Catalyst", Gold Bulletin 2001, 34, 117). Interest in gold as a catalyst increased following the discovery that gold catalysts supported on various metal oxides were highly active for the low temperature oxidation of hydrogen and carbon monoxide (M. Haruta, et al., J. Catal. 1989, 115, 301). Gold catalysts seem to be most useful in oxidation type reactions, particularly CO oxidation. For example, U.S. Pat. No. 4,756,000 describes the use of a gold catalyst for the oxidation of CO at ambient temperatures. U.S. Pat. No. 5,550,093 describes a method for the preparation of a gold catalyst for the oxidation of carbon monoxide. U.S. Pat. No. 5,895,772 describes a catalyst composition containing gold, zirconium oxide and/or cerium oxide support with a transition metal spinel for the oxidation of carbon monoxide. U.S. Pat. No. 4,154,762 describes gold plated wire gauze with less than 2 $m^2/g$ surface area for the oxidative dehydrogenation of aldehydes and ketones.

There are relatively few examples of the utilization of gold catalysts in reduction and hydrogenation reactions. For example, U.S. Pat. No. 4,299,800 illustrates the use of a gold catalyst for the selective reduction/hydrogenation of oxygen in an olefin stream. U.S. Pat. No. 5,506,273 illustrates the use of gold and metal oxide catalyst for the hydrogenation of CO and $CO_2$ to produce methanol and hydrocarbons. However, neither patent teaches or suggests that gold can be used to selectively hydrogenate unsaturated hydrocarbons in a hydrocarbon mixture. Recently, a gold catalyst supported on alumina demonstrated selective hydrogenation of acetylene in ethylene (Jia, et al., "Selective Hydrogenation of Acetylene over $Au/Al_2O_3$ catalyst," *J. Phys. Chem.* pp. 11153–11156 (2000)). However, the catalyst showed good selectivity only at high gold concentrations (10%) and only on relatively low surface area support materials, such as alumina powder having a surface area of about 100 $m^2/g$.

We have discovered that low concentrations of gold (<0.5%) when deposited in high surface area supports (>150 $m^2/g$), produce a catalyst with good catalytic activity for acetylene hydrogenation under commercial conditions. We have also discovered that further performance improvements can be obtained with the inclusion of small quantities of a noble metal, preferably palladium, added to the formulation as an additive for the gold of the catalyst.

Accordingly, it is an object of this invention to disclose a catalyst useful for the selective hydrogenation of a $C_2$ and $C_3$ olefinic feed stream containing acetylenic impurities, particularly for ethylene purification.

It is a still further object of this invention to disclose a catalyst that is useful for front-end selective hydrogenation of acetylenic impurities, whereby the quantity of desirable $C_2$ and $C_3$ olefins, particularly ethylene, is not substantially reduced.

It is a still further object of this invention to disclose a catalyst that is useful for tail-end selective hydrogenation of a $C_2$ and $C_3$ olefinic feed stream containing acetylenic impurities, particularly for ethylene purification.

It is a still further object of the invention to disclose a catalyst containing gold supported on a high surface area inorganic support for use in the selective hydrogenation of acetylenic impurities in ethylene purification.

It is a still further object of the invention to disclose a catalyst containing gold supported on a high surface area inorganic support with a palladium additive for use in the selective hydrogenation of acetylenic impurities for ethylene purification.

It is a still further object of the invention to disclose a process for the production of a gold catalyst placed on a high surface area inorganic support with a noble metal additive for use in the selective hydrogenation of acetylenic impurities in an ethylene purification reaction.

It is a still further object of the invention to disclose a gold impregnated catalyst with a high surface area inorganic support with a noble metal additive for the selective hydrogenation of acetylene which exhibits enhanced selectivity, resistance to run-away, tolerance to CO concentration swings and improved performance at high gas hourly space velocity over conventional palladium and palladium/silver selective hydrogenation catalysts.

These and other objects can be obtained by the selective hydrogenation catalyst and the process for the preparation and use of the selective hydrogenation catalyst for use in a $C_2$ and $C_3$ olefinic feed stream containing acetylenic impurities particularly for ethylene purification, which are disclosed by the present invention.

SUMMARY OF THE INVENTION

The present invention is a catalyst for the selective hydrogenation of acetylenic impurities for ethylene purification, the catalyst comprising from about 0.05 to about 5 weight percent gold incorporated into a high surface area inorganic support, wherein the surface area of the support is at least about 150 $m^2/g$. Optionally, from about 0.001 to about 0.05 weight percent of a noble metal additive is added to the gold catalyst, wherein the noble metal is selected from the group consisting of rhenium, ruthenium, rhodium, osmium, palladium, platinum and iridium. In one composition, the noble metal is preferably palladium, platinum, rhenium or ruthenium, and most preferably is palladium. Preferably, at least about 90 percent of the gold and noble metal additive are deposited within about 250 microns of the surface of the catalyst. Preferably the ratio of the gold to the noble metal additive is at least about 1:1 and more preferably at least about 2:1.

The present invention is also a process for the production of a catalyst for the selective hydrogenation of acetylenic impurities for ethylene purification comprising preparing a high surface area carrier material in a suitable shape, wherein the surface area of the carrier material is at least about 150 $m^2/g$, and impregnating the carrier with a gold compound, wherein the quantity of the gold present in the catalyst comprises from about 0.05 to about 5.0 weight percent. Preferably at least about 90 percent of the gold is located within about 250 microns of the surface of the catalyst.

The process for the production of the catalyst of the invention preferably comprises further impregnating the gold impregnated carrier with a noble metal additive, wherein the amount of the noble metal additive present in the catalyst comprises from about 0.001 to about 0.05 weight percent of the catalyst. Preferably the ratio of the gold to the noble metal additive is at least about 1:1 and more preferably at least about 2:1.

The invention further comprises a process for the selective hydrogenation of acetylenic impurities for both front-end and tail-end ethylene purification comprising passing an ethylene feed stream, which contains acetylenic impurities, over the catalysts described above.

DETAILED DESCRIPTION

The invention is a catalyst for the selective hydrogenation of acetylene for ethylene purification. The invention further comprises a process of hydrogenation of acetylene for ethylene purification using the catalyst of the invention. The invention further comprises a process for the production of the catalyst that is useful for the selective hydrogenation of acetylene for ethylene purification.

It has been surprisingly discovered that a selective hydrogenation catalyst can be produced when gold is incorporated into a high surface area inert carrier. The catalyst carrier may be any high surface area catalyst carrier, such as alumina, silica-alumina, zinc oxide, nickel spinel, titania, zirconia, ceria, chromia-alumina, magnesium oxide, cerium oxide and mixtures thereof. The preferred carrier is high surface area alumina. To qualify as a "high surface area carrier," the carrier must have a surface area greater than about 150 $m^2/g$, preferably from about 150 to about 1000 $m^2/g$, more preferably from about 175 to about 500 $m^2/g$, and most preferably from about 200 to about 300 $m^2/g$. The pore volume of the carrier is preferably in the range of about 0.2 to about 0.6 cc/g.

The catalyst carrier can be formed in any suitable shape, such as a sphere, cylinder, trilob, tablet and the like. In a preferred embodiment the catalyst carrier is a sphere. The catalyst carrier can be formed in any suitable size, preferably from about 1 to about 8 millimeters in diameter.

The gold can be introduced into the high surface area catalyst carrier by any conventional procedure which produces the proper gold loading. One preferred technique involves impregnating the catalyst carrier with an aqueous solution of a gold compound, such as gold chloride ($AuCl_3$).

Preferably, the depth of penetration of the gold compound into the carrier should be controlled so that approximately 90 percent of the gold compound is contained within about 250 microns of the surface of the catalyst carrier. Any suitable method can be used to control gold penetration, such as is disclosed in U.S. Pat. Nos. 4,484,015 and 4,404,124, which patents are incorporated herein by reference.

After gold impregnation, the impregnated catalyst is calcined at a temperature from about 100° C. to about 600° C., preferably for about three hours. The gold compound contained in the gold catalyst precursor is then reduced, preferably by wet reducing, using a suitable wet reducing medium such as sodium formate, formic acid, hydrazine, alkali metal borohydrides, formaldehyde, ascorbic acid, dextrose and other conventional wet reducing agents.

Once the catalyst material has been reduced, it is washed with deionized water to remove any halides, such as chlorides, to a level of less than about 100 ppm. The reduced catalyst composition is then dried at about 100° C. to 600° C.

The gold impregnated catalyst may then be utilized for the selective hydrogenation of acetylene in an olefinic feed stream without further processing. However, in a preferred embodiment at least one additive is added to the gold impregnated catalyst to improve its performance. In a more preferred embodiment, once the gold-impregnated catalyst composition has been calcined, it is impregnated with a noble metal compound as an additive. The noble metals that may be used include palladium, platinum, rhenium, ruthenium, osmium, iridium and rhodium and a combination thereof. In a preferred embodiment the noble metal is selected from the group consisting of palladium, platinum, rhenium and ruthenium, most preferably palladium. The noble metal additive can be impregnated in the gold catalyst by any conventional process such as the same process used for impregnating the gold into the high surface area catalyst carrier. After impregnation, the gold impregnated catalyst material with noble metal additive is then calcined at a temperature from about 100 to about 600° C. for about three hours.

The amount of gold present on the catalyst is from about 0.05 to about 5.0 weight percent, preferably 0.05 to 0.5 weight percent, based on the total weight of the catalyst. The amount of the noble metal additive that may be added is from about 0.005 to about 0.05 weight percent, preferably 0.005 to about 0.03 weight percent, based on the total weight of the catalyst. Preferably the ratio of the gold present on the catalyst to the noble metal additive is greater than 1:1 and more preferably greater than 2:1.

Following the final drying step, the gold catalyst with noble metal additive is ready for use in a hydrogenation reactor, for example for the hydrogenation of acetylene.

The gold catalyst of the invention is designed primarily for the selective hydrogenation of acetylenes in admixture with ethylene. When the process is a front end selective hydrogenation feed stream, the stream normally includes substantial quantities of hydrogen, methane, ethane, ethylene, small quantities of carbon monoxide and carbon dioxide, as well as various impurities, such as acetylene and dienes. In addition to utilization for front-end selective hydrogenation, the gold catalyst of the invention is also useful for tail-end ethylene purification. The goal of the selective hydrogenation reaction is to reduce substantially the amount of the acetylene present in the feed stream without substantially reducing the amount of ethylene that is present.

In use, the gold catalyst is placed in a reactor. The inlet temperature of the feed stream in the reactor is raised to a level sufficient to hydrogenate the acetylene. Generally, this temperature is from about 35° C. to about 100° C. Any suitable reaction pressure can be used. Generally, the total pressure is in the range of about 600 to 6750 kPa with the gas hourly space velocity (GHSV) in the range of about 1000 to about 14000 liters per liter of catalyst per hour. Existing selective hydrogenation catalysts do not perform consistently over this wide range of space velocities in front-end reactor systems. By the process of this invention, enhanced reduction of acetylene to less than 1 ppm is possible with enhanced selectivity and resistance to runaway even when the quantity of the acetylene present in the feed stream prior to hydrogenation is as high as 2–4% by weight.

The gold catalyst of the invention can also be used for tail-end selective hydrogenation reactions and performs better than conventional selective hydrogenation catalysts.

Regeneration of the gold catalyst may be accomplished by heating the catalyst in air at a temperature, preferably not in excess of 500° C., to burn off any organic material, polymers or char.

EXAMPLES

Example 1 (Comparative)

A commercially available, palladium/alumina catalyst manufactured by Süd-Chemie Inc. under the product name G-83A was obtained. Analysis showed that the catalyst contained 0.018 weight percent palladium on an alumina carrier. The carrier for the catalyst had a BET surface area of 3.7 $m^2/g$.

Example 2 (Comparative)

A commercially available catalyst manufactured by Süd-Chemie Inc. under the product name of G-83C was obtained. Analysis showed that the catalyst contained 0.018 weight percent of palladium and 0.07 weight percent of silver on an alumina carrier. The carrier for the catalyst had a BET surface area of about 4.3 $m^2/g$.

Example 3 (Comparative)

Another catalyst was prepared which contained the same composition as Example 2 except the BET surface area of the carrier of the catalyst was about 50 $m^2/g$.

Example 4

A catalyst is prepared by dipping 100 grams of commercially available alumina spheres with a BET surface area of about 250 $m^2/g$ in a $AuCl_3$ solution of sufficient concentration to yield a gold loading of 0.5 weight percent with a gold depth of penetration controlled to wherein at least about 90 percent of the gold is within about 250 microns of the surface of the spheres. After gold impregnation, the catalyst is calcined at 250° C. for about 3 hours. The catalyst is then wet reduced in a 5 percent aqueous sodium formate solution heated to a temperature of about 170° F. (76° C.) for about one hour. The catalyst is then washed free of chlorides (less than 100 ppm) with deionized water at about 160° F. (71° C.). The catalyst is then dried at about 250° F. (121° C.) for about 18 hours.

Example 5

A catalyst is prepared according to the procedure of Example 4 except the aluminum spheres are dipped so as to yield a gold loading of about 0.2 weight percent, and after gold impregnation, the intermediate catalyst is calcined at about 454° C. for about 3 hours. The catalyst is wet reduced, washed, and dried as in Example 4. The gold containing catalyst is then impregnated with palladium by dipping the catalyst spheres in a palladium chloride solution of sufficient concentration to yield a palladium loading of 0.01 weight percent with a palladium depth of penetration controlled to wherein at least about 90 percent of the palladium was within 250 microns of the surface of the spheres. The catalyst is then calcined at 454° C. for three hours.

Example 6

A catalyst is prepared according to the procedure of Example 5 except the aluminum spheres are dipped so as to yield a gold loading of about 0.5 weight percent, and after gold impregnation the catalyst is calcined at about 450° C. for about 3 hours, and the catalyst spheres are dipped in a palladium chloride solution of sufficient concentration to yield a palladium loading of 0.005 weight percent.

Example 7

A catalyst is prepared according to the procedure of Example 5 except after gold impregnation the catalyst is calcined at about 450° C. for about 3 hours.

Example 8

A catalyst is prepared according to the procedure of Example 6 except the aluminum spheres are dipped so as to yield a gold loading of about 0.1 weight percent, and the catalyst spheres are dipped in a palladium chloride solution of sufficient concentration to yield a palladium loading of 0.03 weight percent.

Performance Testing:

Table I, which follows, provides a comparison of the performance of Examples 1, 2 and 3 (Comparative Examples) with Examples 4 through 8 of the invention. The Examples were compared by passing a conventional front-end acetylene reactor feed stream over the catalysts. The catalysts were evaluated in a bench scale laboratory, one-half inch i.d. reactor tube, with a laboratory prepared simulated front-end feed stock.

For each catalyst, the inlet temperature was recorded when less than 25 ppm acetylene leakage was detected at the reactor outlet. This temperature, $T_1$, was designated as the lower reaction temperature for catalyst activity. The inlet temperature was then increased until "run-away" was observed. "Run-away" or thermal excursion is defined as a greater than 4 percent $H_2$ loss in the system, and occurs when the hydrogenation of ethylene ($C_2H_4$) is significant. The temperature of the reactor inlet when run-away was noted is reported as $T_2$. The catalyst activity then is evaluated in terms of the temperature range over which the catalyst could effectively function, or the temperature at which hydrogenation is first observed ($T_1$) to the temperature at which run-away occurs ($T_2$). A large delta T ($T_2-T_1$) indicates that the catalyst can operate effectively over a broad temperature range.

As the reactor inlet temperature is increased, the hydrogenation reaction becomes more active with a greater amount of $C_2H_2$ being hydrogenated and hence, removed from the product stream. However, some hydrogenation of $C_2H_4$ also occurs indicating a loss of selectivity for the reaction. As reported in Table I, "selectivity" of each catalyst is reported as a percentage and is determined by the following calculation: 100 times ((inlet $C_2H_2$–outlet $C_2H_2$) minus ($C_2H_6$ outlet minus $C_2H_6$ inlet))/($C_2H_2$ inlet minus $C_2H_2$ outlet). Higher positive percentages indicate a more selective catalyst. Data was obtained at a moderate GHSV (7000).

TABLE I

7000 GHSV activity/selectivity test

| Run | Catalyst | $T_1$ | $T_2$ | Activity Range $T_2-T_1$ | Selectivity at $T_1$ |
|---|---|---|---|---|---|
| Example 1 | G83A (SCI) Pd/Al$_2$O$_3$ low SA carrier | 140° F. (60° C.) | 150° F. (65.5° C.) | 10 | 3% |
| Example 2 | G83C (SCI) Pd/Ag/Al$_2$O$_3$ low SA carrier | 115° F. (46.1° C.) | 125° F. (51.6° C.) | 10 | −125% |
| Example 3 | Pd/Ag/Al$_2$O$_3$ medium SA carrier | 132° F. (55.5° C.) | 145° F. (62.8° C.) | 13 | −101.9% |
| Example 4 | Au/Al$_2$O$_3$ | 201° F. (93.8° C.) | —[a] | — | 41.9% |
| Example 5 | Au/Pd/Al$_2$O$_3$ high SA carrier | 131° F. (55° C.) | 154° F. (67.8° C.) | 23 | 64.4% |
| Example 6 | Au/Pd/Al$_2$O$_3$ high SA carrier | 148° F. (64.5° C.) | 184° F. (84.5° C.) | 36 | 51.7% |
| Example 7 | Au/Pd/Al$_2$O$_3$ high SA carrier | 122° F. (49.8° C.) | 144° F. (62.3° C.) | 22 | 46.5% |
| Example 8 | Au/Pd/Al$_2$O$_3$ high SA carrier | 104° F. (40° C.) | 117° F. (47.2° C.) | 13 | 59.1% |

[a]No runaway observed

Comparison of the activity range and the selectivity for the prior art catalysts (Examples 1–3) to the inventive catalysts (Examples 4–8) demonstrates the enhanced performance of the catalysts of the invention. Selectivity is significantly improved relative to the prior art catalysts. Further, the catalysts of the invention demonstrate a broader temperature range over which the catalysts are active for hydrogenation than the prior art catalysts.

The principles, preferred embodiments, and modes of operation of the present invention have been described in the foregoing specification. The invention which is intended to be protected herein, however, is not to be construed or limited to the particular terms of disclosure, as these are to be regarded as being illustrative, rather than restrictive. Variations and changes may be made by those skilled in the art without departing from the spirit of the invention.

What is claimed is:

1. A catalyst for the selective hydrogenation of acetylene, said catalyst comprising a high surface area inorganic support material, wherein the surface area is at least about 150 m$^2$/g, and gold, wherein the gold comprises from about 0.05 to about 5.0 weight percent of the catalyst and wherein the depth of penetration of the gold into the support material is such that at least about 90 percent of the gold is located within about 250 microns of the surface of the catalyst, wherein the weight percentages are based on the total weight of the catalyst.

2. The catalyst of claim 1 wherein the inorganic support material is selected from the group consisting of high surface area alumina, silica-alumina, zinc oxide, nickel spinel, titania, zirconia, ceria, chromia-alumina, magnesium oxide, and mixtures thereof.

3. The catalyst of claim 1 formed in a shape selected from the group consisting of a sphere, trihole, monolith, pellet and tablet.

4. The catalyst of claim 3 wherein the shape of the catalyst is a sphere with a diameter in the range from about 1 millimeter to about 8 millimeters.

5. The catalyst of claim 1 wherein the concentration of the gold in the catalyst is from about 0.05 to about 0.5 weight percent, based on the total weight of the catalyst.

6. The catalyst of claim 1 wherein the surface area of the inorganic support material is from about 200 $m^2/g$ to about 300 $m^2g$.

7. A catalyst for the selective hydrogenation of acetylene comprising a high surface area inorganic support material, wherein the surface area is at least about 150 $m^2/g$, gold, wherein the gold comprises from about 0.05 to about 5.0 weight percent of the catalyst, and an additive comprising from about 0.001 to about 0.05 weight percent of a noble metal, wherein the noble metal is selected from the group consisting of rhenium, ruthenium, rhodium, platinum, palladium, osmium, iridium and combinations thereof, and wherein at least about 90 percent of the noble metal additive is located within about 250 microns of the surface of the catalyst.

8. The catalyst of claim 7 wherein the noble metal additive is selected from the group consisting of palladium, platinum, rhenium and ruthenium.

9. The catalyst of claim 7 wherein the noble metal additive comprises palladium.

10. The catalyst of claim 7 wherein the concentration of the noble metal additive in the catalyst is from about 0.005 to about 0.02 weight percent.

11. The catalyst of claim 7 wherein the surface area of the inorganic support material is from about 200 $m^2/g$ to about 300 $m^2/g$.

12. The catalyst of claim 7 wherein the ratio of the gold to the noble metal additive in the catalyst calculated as elements, is at least about 1:1.

13. The catalyst of claim 7 wherein the ratio of the gold to the noble metal additive in the catalyst calculated as elements, is at least about 2:1.

14. The catalyst of claim 7 formed in a shape selected from the group consisting of a sphere, trihole, monolith, pellet and tablet.

15. The catalyst of claim 14 wherein the shape of the catalyst is a sphere with a diameter in the range from about 1 to about 8 millimeters.

16. A process for the manufacture of a catalyst for the selective hydrogenation of acetylene comprising
preparing a high surface area catalyst support wherein the surface area of the catalyst support is at least about 150 $m^2/g$,
impregnating the catalyst support with a gold metal source, wherein the concentration of the gold in the catalyst is from about 0.05 to about 5.0 weight percent, such that the depth of penetration of the gold into the catalyst support is within about 250 microns of the surface of the catalyst,
reducing the gold impregnated catalyst, and
washing and drying the reduced catalyst.

17. The process of claim 16 further comprising impregnating the catalyst with a noble metal additive source, reducing the noble metal additive source, washing and drying the reduced catalyst to produce the catalyst, wherein the concentration of the noble metal additive in the catalyst is from about 0.001 to about 0.05 weight percent, and wherein the noble metal additive is selected from the group consisting of rhenium, ruthenium, rhodium, platinum, palladium, osmium and iridium.

18. The process of claim 17 wherein the noble metal additive is selected from the group consisting of palladium, platinum, rhenium and ruthenium.

19. The process of claim 17 wherein the noble metal additive comprises palladium.

20. The process of claim 17 wherein the catalyst comprises from about 0.05 to about 0.5 weight percent gold and from about 0.005 to about 0.03 weight percent of a noble metal additive.

* * * * *